United States Patent [19]

Simpson

[11] Patent Number: 4,936,016
[45] Date of Patent: Jun. 26, 1990

[54] METHOD AND APPARATUS FOR MEASURING DISPERSIVE CONDITION OF OIL

[75] Inventor: George Simpson, Derby, England
[73] Assignee: The Lubrizol Corporation, Wickliffe, Ohio
[21] Appl. No.: 234,350
[22] Filed: Aug. 19, 1988

Related U.S. Application Data

[63] Continuation of Ser. No. 66,904, Jun. 25, 1987, abandoned.

[51] Int. Cl.$^5$ ............................................. G01N 33/30
[52] U.S. Cl. ........................... 33/1 BB; 33/555.2; 73/61.2; 73/64
[58] Field of Search ............... 33/178 B, 562, 563, 33/565, 1 B, 1 BB, 1 C, 555.1, 555.2; 73/64, 61.2

[56] References Cited

U.S. PATENT DOCUMENTS

| | | | |
|---|---|---|---|
| 1,403,677 | 1/1922 | Faas | 33/1 BB |
| 2,302,224 | 11/1942 | Jones | 73/64 |
| 2,622,471 | 12/1952 | Spaeks | 73/64 |
| 2,702,944 | 3/1955 | Lane et al. | 33/1 B |
| 2,728,145 | 12/1955 | Holladay | 33/178 B |
| 3,049,964 | 8/1962 | Miller et al. | 73/64 |
| 4,697,346 | 10/1987 | Warbury | 33/1 BB |

FOREIGN PATENT DOCUMENTS 941520 4/1956 Fed. Rep. of Germany .......... 73/64

OTHER PUBLICATIONS

Rapid Design Inc. Catalogue, No. 5: No. 40 Circle Template.
American Machinist, "Lathe and Drill Gage", Dawn Crafts Co., Buffalo, NY, Jan. 13, 1958, p. 170.

Primary Examiner—Thomas B. Will
Attorney, Agent, or Firm—Joseph P. Fischer; Frederick D. Hunter; Robert A. Franks

[57] ABSTRACT

A template for use in evaluating the dispersive condition of a lubricating oil is provided. A method employing the template and an absorbent material onto which a sample of oil is placed, and measuring undispersed components of the oil on the absorbent material, is described. A kit which comprises the template and the absorbent material for use in the method of this invention is also described.

6 Claims, 2 Drawing Sheets

METHOD AND APPARATUS FOR MEASURING DISPERSIVE CONDITION OF OIL

This is a continuation of co-pending application Ser. No. 066,904, filed June 25, 1987, now abandoned.

FIELD OF THE INVENTION

This invention relates to lubricating oils. In particular, this invention relates to methods for evaluating the dispersive condition of lubricating oils, and provides an apparatus for use in the method.

BACKGROUND OF THE INVENTION

Over the years, various means for monitoring and determining the condition of used lubricating oils have been developed. Such methods have been used by workers involved in the development of lubricants and additives therefor, by equipment manufacturers and by operators of equipment in the field. Such tests include acid number, wear metal content, color, change in viscosity with time and the like.

A test which has been used to determine the dispersive condition of a used oil, either a test oil or one which has been used in field service, is to assess the appearance of a spot of the oil which has been placed on an absorbent material. This method involves placing a measured drop of the oil on a sheet of absorbent material, usually a material such as chromatography paper, allowing the spot to develop, then examining the spot for the presence of undispersed sludge. The oil sample appears as a circular spot on the absorbent material. As the oil is absorbed it will form a particular and characteristic pattern. This pattern is then interpreted to determine the condition of the oil. One such test, which involves only a visual assessment of the oil spot, is described in C. A. Bailey and J. S. Aarons, "The Lubrication Engineers Manual", First Edition, United States Steel Corporation, pages 72-73 (1971).

Visual interpretation of the oil spots can provide a qualitative assessment of the condition of the oil sample. However, it has been found that the size of the components of the oil spot provide considerable information regarding the oil condition. In the past, workers generally have measured the approximate diameter of the various components of the oil spot using a ruler or other simple measuring device. There exists a need for a simpler, quantitative method for measuring the oil spots, assigning a pass or fail rating to same, and classifying the relative performance of various oils.

SUMMARY OF THE INVENTION

It is a general object of the present invention to provide a meaningful test to quantify the sludging properties of used oils. This test is based on the well-known spot technique described hereinabove, often referred to as the blotter spot technique. A further object is to provide apparatus to be used in the method for determining the sludging properties and the extent of deterioration and contamination of a lubricating oil.

The above objects are accomplished by providing a template which comprises a planar member constructed from a translucent or transparent material and having a flat planar surface, said planar member including an array of circles of different diameters spaced side-by-side along a common centerline on said planar surface, the largest circle in said array being at or near one end of said planar surface and the smallest circle in said array being at or near the other end of said planar surface, the circles between said largest circle and said smallest circle in said array being progressively smaller when moving from said largest circle to said smallest circle, each circle having a characteristic identifying symbol in sufficiently close proximity to identify said circle and distinguish said circle from the other circles in said array. The circles may be cut through the planar member and removed resulting in circular holes in the planar member. The above described template may be included in a kit for measuring the dispersive condition of an oil comprising:

a flat absorbent material for receiving a test sample of said oil; and a template for measuring the size of any undispersed part of said oil, said template comprising a planar member constructed from a transparent or translucent material and having a flat planar surface, said planar member including an array of circles of different diameters spaced side-by-side along a common centerline on said planar surface, the largest circle in said array being at or near one end of said planar surface and the smallest circle in said array being at or near the other end of said planar surface, the circles between said largest circle and said smallest circle in said array being progressively smaller when moving from said largest circle to said smallest circle, each circle having a characteristic identifying symbol in sufficiently close proximity to identify said circle and distinguish said circle from the other circles in said array.

The method for accomplishing these object involves (A) placing a sample of oil on a flat absorbent material;

(B) heating said sample at a sufficient temperature for an effective period of time while maintaining said absorbent material in a horizontal or substantially horizontal position to develop a circular spot on said absorbent material;

(C) locating any relatively darkened section within said circular spot;

(D) placing a template over said relatively darkened section and aligning said relatively darkened section with a circle on said template having the same or substantially same size, said template comprising a planar member constructed from a transparent or translucent material and having a flat planar surface, said planar member including an array of circles of different diameters spaced side-by-side along a common centerline on said planar surface, the largest circle in said array being at or near one end of said planar surface and the smallest circle in said array being at or near the other end of said planar surface, the circles between said largest circle and said smallest circle in said array being progressively smaller when moving from said largest circle to said smallest circle, each circle having a characteristic identifying symbol in sufficiently close proximity to identify said circle and distinguish said circle from the other circles in said array; and (E) assigning a rating to said sample corresponding to the identifying mark assigned to the circle aligned with said darkened section in step D).

The template used in this method may be as described hereinabove. The absorbent material used in the method is often chromatography paper.

DESCRIPTION OF THE DRAWINGS

In the annexed drawings, like part and features are designated by like references.

DETAILED DESCRIPTION OF THE INVENTION

Figure 1:
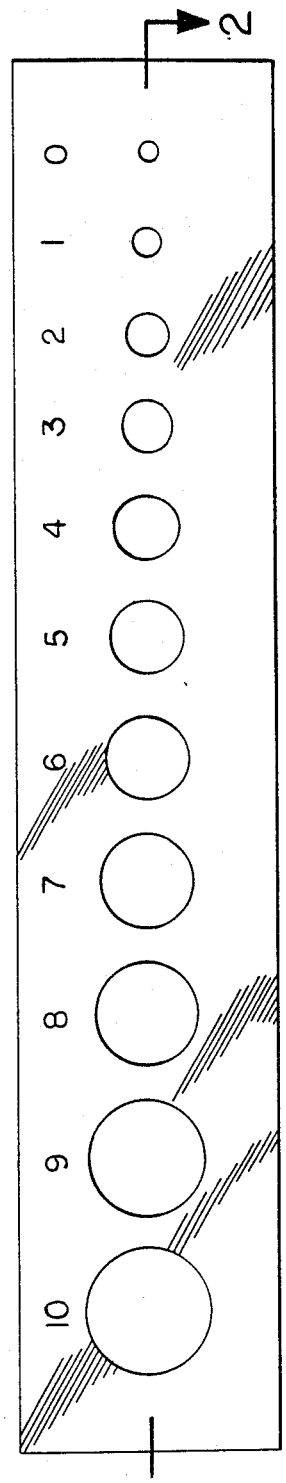
FIG. 1 is a plan view of a template embodying the present invention in a particular form.

As described hereinabove, this invention provides a method for determining the dispersive condition of a lubricating oil. Briefly, the invention is for a method and apparatus for determining the dispersive condition of a lubricating oil by measuring the extent of deterioration and contamination of the oil employing an oil spot test, and measuring the oil spots employing a template as described in greater detail hereinbelow.

THE TEMPLATE

The method of this invention involves employing a template which is used for measuring the extent of deterioration and contamination of a lubricating oil, which template comprises a planar member constructed from a translucent or transparent material, and having a flat planar surface, said planar member including an array of circles of different diameters spaced side-by-side along a common centerline on said planar surface, the largest circle in said array being at or near one end of said planar surface and the smallest circle in said array being at or near the other end of said planar surface, the circles between said largest circle and said smallest circle in said array being progressively smaller when moving from said largest circle to said smallest circle, each circle having a characteristic identifying symbol in sufficiently close proximity to identify said circle and distinguish said circle from the other circles in said array. The number of circles to be inscribed in the template will depend on a number of factors. For example, a template having a single circle which corresponds to the pass-fail threshold for a particular set of test conditions could be useful, but would not permit the user to readily classify the relative performance of several samples run on a particular test. A template having a sufficient number of circles ranging over a reasonably broad range of sizes would permit the template to be used not only to classify the relative performance of materials on a particular test, but also would usually allow a single template to be used for tests run under a variety of test conditions. A useful template will usually have at least 3 circles thereon. Often the template will have from 3 to 20 circles, more often from 5 to 15 circles.

The arrangement of the circles is important in order to facilitate use of the template. Usually the circles are arranged in some logical fashion, such as from smallest to largest along the length of the template. Particularly convenient is an arrangement wherein circles are inscribed on said planar member along a common center line, the largest circle being inscribed near one end of said planar member and the smallest circle being inscribed near the other end of said planar member, the diameter of each circle being progressively smaller than the next adjacent circle when moving from said largest circle to said smallest circle.

The size and shape of the template is not critical. Both of these features will be determined by the number and size of the circles inscribed on the template. Generally, the template will be of such a size and shape as to be convenient for use. To accommodate a plurality of circles, the template is often an elongated, usually rectangular shape.

The circles which have been inscribed onto the planar member may be drawn or etched thereon or may be cut through the planar member and removed from the planar member resulting in circular holes in the planar member.

Figure 2:
FIG. 2 is a view in section taken along line 2—2 of FIG. 1.

The template is preferably constructed from a translucent or transparent material. When the holes are simply drawn or etched onto the template, the template must be constructed of a translucent or transparent material in order to allow the user of the template to observe the test specimen through the template and to align the spots on the test specimen with the circles on the template. When the circles are cut through the planar member and removed from the planar member resulting in circular holes in the in planar member, the template may be constructed of any convenient material, transparent, translucent or opaque. However, it has been found that a transparent or translucent material provides a template which is most convenient in use. Accordingly, except when the template must be constructed of a translucent or transparent material, the template may be constructed of materials such as plastic, wood, paper or metal. For the sake of durability and ease of use, it is preferred that the template be constructed of an essentially transparent material such as Lucite ® plastic sheet. The thickness of the template as represented by FIG. 2 will be determined by the preference of the user. Thus, the template may be essentially paper-thin, or of any thickness that provides a template of the desired utility, transparency and durability. For ease of use and storage, the template is normally no thicker than is required to provide dimensional stability.

The characteristic identifying symbols provide a means for classifying the spots on the test specimen. All that is required is that the characteristic identifying symbols for each circle is located in sufficiently close proximity to identify said circle, and each of said symbols is different from any other of said symbols. For convenience sake, letters of the alphabet or Arabic numerals are usually used as the characteristic identifying symbols. When letters of the alphabet or Arabic numerals are used, they are usually associated with the circles in some logical fashion, such as the highest numeral being associated with the largest circle and progressing to the lowest numeral being associated with the smallest circle.

The Test Specimen

The test specimen is an absorbent material. Any absorbent material which retains a measured sample of oil, and permits the oil sample to develop into the characteristic pattern described hereinbelow may be used. Such materials may include pieces of cloth, paper, especially blotter paper or chromatography paper or chromatographic slides. Chromatography paper is preferred. Particularly useful chromatography paper is that identified as Whatman 1 Chromatography paper and supplied by Whatman Ltd, England. However, as mentioned hereinabove, other absorbent material may be used provided it can be obtained in a consistent quality such that satisfactory repeatability of test results can be obtained.

The Method

The method of this invention comprises (A) placing a sample of oil on a flat absorbent material;

(B) heating said sample at a sufficient temperature for an effective period of time while maintaining said absorbent material in a horizontal or substantially horizontal position to develop a circular spot on said absorbent material;

(C) locating any relatively darkened section within said circular spot;

(D) placing a template over said relatively darkened section and aligning said relatively darkened section with a circle on said template having the same or substantially same size, said template comprising a planar member constructed from a transparent or translucent material and having a flat planar surface, said planar member including an array of circles of different diameters spaced side-by-side along a common centerline on said planar surface, the largest circle in said array being at or near one end of said planar surface and the smallest circle in said array being at or near the other end of said planar surface, the circles between said largest circle and said smallest circle in said array being progressively smaller when moving from said largest circle to said smallest circle, each circle having a characteristic identifying symbol in sufficiently close proximity to identify said circle and distinguish said circle from the other circles in said array; and (E) assigning a rating to said sample corresponding to the identifying mark assigned to the circle aligned with said darkened section in step (D).

As mentioned hereinabove, the template and the absorbent material may be of any particular design and material as provides ease of use and satisfactory repeatability of tests. A particularly preferred absorbent material is chromatography paper supplied by Whatman, Ltd as Whatman 1 Chromatography.

The oil sample from which the measured drop of oil to be studied is taken may be from a full scale test engine, an engine in the field, or from a bench test. When the oil is taken from an operating device, such as an internal combustion engine, it is generally necessary that the oil sample be taken while the device is operating, in order to insure a representative sample. Generally, the amount oil used in a bench test is relatively small, often little more than a few cubic centimeters, such that it is only necessary to observe that the test oil is uniform before placing a sample of the oil on the absorbent material.

It is necessary that production of the oil spot be done in a careful and consistent manner. The absorbent material, usually chromatography paper, is placed in a frame or other holder to insure that it is flat. The absorbent material in its holder is then placed in an essentially horizontal position. Approximately 20 microliters (1 drop) of the test oil is placed on the absorbent material. Often the drop of oil is somewhat viscous, and it may be necessary to touch the absorbent material lightly with the drop of oil if it does not fall on its own accord. The spots are then stored for 1 hour at 80–90° C., being sure that the paper remains in a horizontal position. The exterior diameter of the developed spot normally measures 30–35 millimeters. The color of the oil spot will usually indicate the amount of contaminant present in the oil. The contaminant may be dispersed in the oil or it may be deposited as sludge. Oils in excellent dispersive condition give rise to relatively uniform spots which do not have any areas having pronounced differences in appearance. It has been observed that an oil which essentially lacks dispersancy gives rise to an oil spot containing a relatively small, dense, black spot essentially concentric with the main oil spot. The dense, black portion consists of undispersed sludge.

Figure 3:
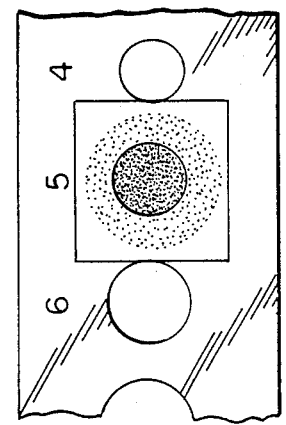
FIG. 3 is a perspective view illustrating the use of the template of FIG. 1 in measuring the dispersive condition of an oil sample.
Figure 4:
FIG. 4 is a view in section taken along line 2—2 of FIG. 1 when the circles are drawn on the template.
Figure 5:
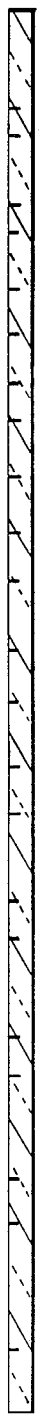
FIG. 5 is a view in section taken along line 2—2 of FIG. 1 when the circles are etched on said planar surface.

It is important to note that it is not the overall size of the oil spot that indicates the dispersive condition of the oil, but rather the darker portion of the oil spot. An oil containing a large amount of contaminants may still be in excellent dispersive condition. In such a case the oil spot will appear very dark in color but will be essentially uniform in intensity. Usually, when the oil is still in good dispersive condition, the oil spot will not be uniform in intensity over the entire area of the spot. In such a case a portion of the oil spot, usually a central area, is darker than the outer perimeter area of the oil spot. However, this darker area is not substantially smaller than the remainder of the oil spot. FIG. 3 illustrates the measurement and classification of a developed oil spot on absorbent material. The portion of the spot measured by the circles of the template is the darker area, centrally located on the main oil spot which is denoted by the lighter shading.

Depending on the test conditions, a pass-fail threshold is assigned. This pass-fail threshold will correspond to a spot having a diameter corresponding to one of the circles on the template. Thus, any spot smaller than the spot corresponding to the pass-fail threshold is considered a fail. Alternatively, any spot larger than the pass-fail threshold spot is considered a pass. The value of having a template with a plurality of circles inscribed thereon is that relative ratings may be assigned. For example, using the template illustrated in FIG. 1, assuming that a spot having a size corresponding to circle 5 is considered a pass, any spot larger than circle 5 is considered a pass. Likewise, any spot smaller than that corresponding to circle 5 is considered a fail. However, an oil providing a spot corresponding to circle 8 is generally considered to be superior to oil providing a spot corresponding to circle 6, although both are considered to be pass oils.

As mentioned hereinabove, the oil spot may appear as an essentially uniform dispersion of oil and contaminant. As the amount of contaminants increases, which is often accompanied by a decrease in dispersancy, the oil spot will begin to take on the appearance of concentric circles. Undispersed contaminants (sludge) appear as a darker spot concentric with, but somewhat smaller in diameter than, the oil spot. The darker spot is coagulated sludge. In general, the smaller the difference in size between the main oil spot and the smaller, usually darker spot concentric with the larger oil spot, the better the condition of the test oil.

As mentioned hereinabove, the method of this invention and the template used therein are useful to determine the condition of a used lubricating oil. The most common application is to determine the dispersive condition of a used crankcase oil. The template and the absorbent material may be supplied together in a kit to be used in the method of this invention.

Using the method and apparatus of this invention, an engine oil sample may also be tested to determine its dispersive condition and its residual dispersive power.

Residual dispersive power is a measure of an oil's ability to continue to provide good dispersancy.

Following a period of exposure to an accelerated dispersancy bench test, samples of a test oil are spotted on chromatography paper, Whatman Chromo 1. The oil spots are developed by heating the spotted chromatography paper is an oven for one hour at 80–90° C. Oil samples found to result in spot diameter greater than 20 cm, corresponding to a dispersancy spot rating greater than 6 on a template so calibrated, are deemed to be "pass" oils with respect to dispersive power.

A small sample of oil (2–3 cm$^3$) is subjected to heat treatment for five minutes at 200° C., then again is tested on the spot test. A spot greater than 15 cm in diameter indicates adequate residual dispersive power.

This test may be used to predict expected performance on the CRC V-D engine test. It has also been found that the apparatus and method of this invention are useful when evaluating the performance of lubricating oils with respect to "Black Sludge" formation in the Daimler-Benz M102E Sludge Test.

What is claimed is:

1. A method for measuring the dispersive condition of an oil comprising:
   (A) placing a sample of said oil on a flat absorbent material;
   (B) heating said sample at a sufficient temperature for an effective period of time while maintaining said absorbent material in a horizontal or substantially horizontal position to develop a circular spot on said absorbent material;
   (C) locating any relatively darkened section within said circular spot;
   (D) placing a template over said relatively darkened section and aligning said relatively darkened section with a circle on said template having the same or substantially same size, said template comprising a planar member constructed from a transparent or translucent material and having a flat planar surface, said planar member including an array of circles of different diameters, drawn thereon, etched thereon or comprising circular holes, spaced side-by-side along a common centerline on said planar surface, the largest circle in said array being at or near one end of said planar surface and the smallest circle in said array being at or near the other end of said planar surface, the circles between said largest circle and said smallest circle in said array being progressively smaller when moving from said largest circle to said smallest circle, each circle having a characteristic identifying symbol in sufficiently close proximity to identify said circle and distinguish said circle from the other circles in said array; and
   (E) assigning a rating to said sample corresponding to the identifying symbol assigned to the circle aligned with said darkened section in step (D).

2. The method of claim 1 wherein the sample of said oil is taken from an operating device while the device is in operation.

3. The method of claim 1 wherein the absorbent material is chromatography paper placed in a frame.

4. The method of claim 1 wherein each of said circles of said template comprises a circular hole in said planar member of said template.

5. The method of claim 1 wherein said planar member of said template comprises an elongated thin piece of plastic material.

6. The method of claim 1 wherein said sample is heated to a temperature in the range of about 80° C. to about 90° C. for about one hour during step (B).

* * * * *